United States Patent [19]

Edge

[11] 4,310,544

[45] Jan. 12, 1982

[54] HYDROXYACETIC ACID DERIVATIVES WITH ANTI-ARTHRITIC PROPERTIES

[75] Inventor: Michael D. Edge, Congleton, England

[73] Assignee: Imperial Chemical Industries Limited, London, England

[21] Appl. No.: 203,225

[22] Filed: Oct. 31, 1980

Related U.S. Application Data

[63] Continuation of Ser. No. 66,469, Aug. 13, 1979, abandoned.

[30] Foreign Application Priority Data

Sep. 8, 1978 [GB] United Kingdom .............. 36173/78

[51] Int. Cl.³ .................. A61K 31/19; A61K 31/235; C07C 69/76; C07C 51/16
[52] U.S. Cl. .................................. 424/308; 424/317; 560/102; 562/409; 562/418
[58] Field of Search ................ 424/308, 317; 560/102; 562/409, 418

[56] References Cited

FOREIGN PATENT DOCUMENTS 1121027 7/1968 United Kingdom .
1140748 1/1969 United Kingdom .
1402446 8/1975 United Kingdom .
1435050 5/1976 United Kingdom .
1098111 1/1978 United Kingdom .
1499508 2/1978 United Kingdom .

*Primary Examiner*—Stanley J. Friedman
*Attorney, Agent, or Firm*—Cushman, Darby & Cushman

[57] ABSTRACT

The invention concerns novel 2-[4-(4-chlorophenyl)-benzyloxy]acetic acids of the formula:

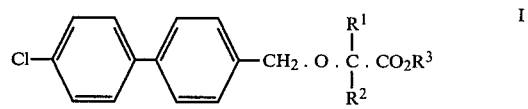

in which $R^1$ is hydrogen or (1–4C)alkyl, $R^2$ is phenyl optionally bearing a halogeno substituent, and $R^3$ is hydrogen or (1–4C)alkyl, and when $R^3$ is hydrogen pharmaceutically acceptable base-addition salts thereof; and processes for their manufacture.

The compounds possess useful anti-arthritic properties coupled with desirable pharmacokinetic properties and the minimum of adverse properties, and the invention also concerns pharmaceutical compositions of such compounds for use in the treatment of arthritic joint diseases. A typical compound of the invention is 2-[4-(4-chlorophenyl)benzyloxy]-2-phenyl propionic acid.

11 Claims, No Drawings

HYDROXYACETIC ACID DERIVATIVES WITH ANTI-ARTHRITIC PROPERTIES

This is a continuation of application Ser. No. 066,469, filed Aug. 13, 1979, now abandoned.

This invention relates to hydroxyacetic acid derivatives and, more particularly, it relates to hydroxyacetic derivatives which possess useful anti-arthritic properties, to pharmaceutical compositions thereof for use in the treatment of arthritic joint diseases, and to processes for the manufacture of said derivatives.

It is known from our earlier work that various 2-(substituted benzyloxy)acetic acids and their 2-trifluoromethyl derivatives lower the level of at least one factor believed to be involved in atherosclerotic disease, for example the level of serum cholesterol, serum triglycerides or plasma fibrinogen, and, in certain cases, also possess anti-arthritic properties. (U.K. patent specification No. 1140748 and No. 1,499,508). It is also known that various 2-(phenoxy)phenylacetic acid derivatives possess hypocholesterolaemic properties (U.K. patent specification No. 1,098,111 and No. 1,435,050). We have now discovered, and herein lies the basis for our invention, that a particular group of novel 2-[4-(4-chlorophenyl)benzyloxy]acetic acids, having certain structural resemblance to the above mentioned known compounds, but bearing an additional 2-phenyl substituent, possess useful anti-arthritic properties coupled with desirable pharmacokinetic properties and the minimum of adverse properties.

According to the invention there is provided a hydroxyacetic acid derivative of the formula:

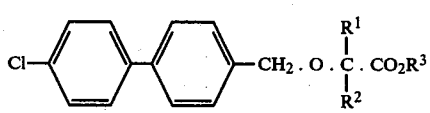

I wherein $R^1$ is hydrogen or a (1–4C)alkyl radical, $R^2$ is a phenyl radical optionally bearing a halogeno radical and $R^3$ is hydrogen or a (1–4C)alkyl radical; or, when $R^3$ is hydrogen, a pharmaceutically acceptable base-addition salt thereof.

It will be apparent that the compounds of formula I contain an asymmetric carbon atom and, as such, can be isolated in a racemic form and in two optically active forms. It is to be understood that this specification is addressed to the racemic form of compounds of formula I and to any optically active form which possesses the above mentioned useful properties; it being a matter of common general knowledge in the art how to resolve a racemic form, or how to synthesise an optical isomer from an optically active starting material, and then to determine the biological properties of the optical isomers.

A particular value for $R^1$ when it is a (1–4C)-alkyl radical is, for example, a methyl or ethyl radical.

A particular value for an optional halogeno radical present on $R^2$ is, for example, a fluoro, chloro or bromo radical.

A particular value for $R^3$ when it is a (1–4C)-alkyl radical is, for example, a methyl or ethyl radical.

A specific value for $R^2$ is, for example, when it is a phenyl, 4-fluorophenyl, 4-chlorophenyl or 4-bromophenyl radical.

A preferred value for $R^3$ is hydrogen.

A preferred group of compounds of the invention comprises those compounds of formula I wherein $R^1$ is a methyl or ethyl radical, $R^2$ is a phenyl radical, and $R^3$ is hydrogen or a methyl or ethyl radical; and, when $R^3$ is hydrogen, the pharmaceutically acceptable base-addition salts thereof.

A further preferred group of compounds of the invention comprises those compounds of formula I wherein $R^1$ has any of the values defined hereinbefore, $R^2$ is a phenyl or 4-chlorophenyl radical, and $R^3$ is hydrogen or a methyl or ethyl radical; and, when $R^3$ is hydrogen, the pharmaceutically acceptable salts thereof.

A particular base-addition salt of a compound of formula I wherein $R^3$ is hydrogen is, for example, an alkali metal or alkaline metal salt, for example a sodium, potassium, calcium or magnesium salt, an aluminium salt, for example an aluminium hydroxide disalt, an ammonium salt, or a salt of an organic base affording a pharmaceutically acceptable cation, for example triethanolamine or tris(hydroxymethyl)methylamine.

Specific compounds of the invention are described hereinafter in the Examples. Of these, particularly preferred compounds of the invention are 2-[4-(4-chlorophenyl)benzyloxy]-2-phenylpropionic acid and 2-[4-(4-chlorophenyl)benzyloxy]-2-phenylbutyric acid, or a pharmaceutically acceptable base-addition salt thereof.

The compounds of formula I may be manufactured by any chemical process which is known to be applicable to the synthesis of chemically analogous compounds. Such processes are provided as a further feature of the invention and are exemplified by the following in which $R^1$, $R^2$ and $R^3$ have any of the above meanings unless otherwise stated:

(a) A base-addition salt of a compound of the formula:

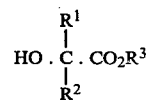

II is reacted with a 4-(4-chlorophenyl)benzyl halide.

A particularly suitable base-addition salt of a compound of formula II is, for example, an alkali metal salt, for example a sodium or potassium salt, or, when $R^3$ is hydrogen is, for example, a di-alkali metal salt, for example a di-sodium or di-potassium salt. The required base-addition salt may conveniently be preformed by reaction of a compound of formula II with a suitable base, for example an alkali metal hydride or (1–4C)alkoxide, for example sodium hydride or ethoxide, conveniently in a suitable solvent which may then function as solvent for process (a). In such cases a suitable solvent when an alkali metal hydride is used as the base, is, for example, dimethyl sulphoxide or dimethylformamide, and when an alkali metal (1–4C)alkoxide is used, is, for example, the corresponding (1–4C)alkanol.

Alternatively, the base-addition salt of the compound of formula II may be formed during process (a) by using a compound of formula II as starting material instead of its salt, and carrying out the reaction with the substituted benzyl halide in the presence of a suitable base and suitable solvent as defined above.

The process may be carried out, for example, at 0° to 100° C., and particularly conveniently, at 15° to 30° C. The process is conveniently performed in a suitable inert solvent, for example dimethylformamide, dimethylsulphoxide, or hexamethylphosphoramide, optionally together with, for example, tetrahydrofuran. Alternatively, a (1–4C)alkanol, for example ethanol, may be used as solvent, it being understood that when $R^3$ is a (1–4C)alkyl radical which does not correspond to the (1–4C)alkanol which is used as solvent, then some ester exchange may occur.

A particularly suitable 4-(4-chlorophenyl)benzyl halide is, for example 4-(4-chlorophenyl)benzyl chloride or bromide.

(b) A base-addition salt of 4-(4-chlorophenyl)benzyl alcohol is reacted with a halogenated compound of the formula:

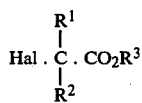
    III wherein Hal. is a chloro, bromo or iodo radical.

A particularly suitable base-addition salt of the substituted benzyl alcohol is, for example, the sodium or potassium salt. This salt is conveniently pre-formed by reaction of 4-(4-chlorophenyl)benzyl alcohol with, for example, the appropriate alkali metal hydride or ethoxide in a suitable solvent, for example dimethyl formamide or ethanol, respectively, as mentioned above for process (a).

Alternatively, as with process (a), the base-addition salt may be formed in situ during process (b) by using 4-(4-chlorophenyl)benzyl alcohol instead of its base-addition salt as starting material, and carrying out the reaction with the halide of formula III in the presence of a suitable base and solvent as defined above.

The process may be carried out at similar temperatures and in similar solvents to those described for process (a) hereinabove. However, it will be recognised that when $R^3$ is hydrogen it is necessary to employ at least two molecular equivalents of the base-addition salt of the substituted benzyl alcohol.

(c) For a compound of formula I wherein $R^3$ is hydrogen, a compound of the formula:

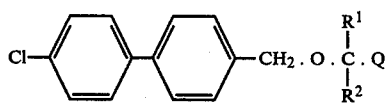
    IV wherein Q is a (1–6C)alkoxycarbonyl, benzyloxycarbonyl, phenoxycarbonyl or cyano radical, is hydrolysed.

A particularly suitable value for Q when it is a (1–6C-)alkoxycarbonyl radical is, for example, a methoxycarbonyl or ethoxycarbonyl radical.

The hydrolysis is conveniently carried out, for example, by reacting the compound of formula IV with a suitable base, for example sodium hydroxide or potassium hydroxide in an organic solvent, for example methanol or ethanol, optionally mixed with water. The hydrolysis may be carried out, for example, at 15° to 100° C., and is particularly conveniently carried out at 60° to 80° C.

The necessary starting materials of formula IV wherein Q is other than a cyano radical may be conveniently obtained using the procedure and general reaction conditions of process (a) but employing 4-(4-chlorophenyl)benzyl chloride and the sodium salt of the appropriate hydroxy compound of the formula:

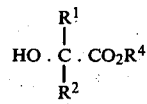
    V wherein $R^4$ is a (1–6C)alkyl, benzyl or phenyl radical, as reactants.

The corresponding cyano compounds of formula IV may be obtained in a similar manner but replacing the sodium salt of the hydroxy compound of formula V by the sodium salt of a compound of the formula:

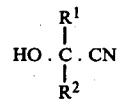
    VI (d) For a compound of formula I wherein $R^3$ is a (1–4C)alkyl radical, a compound of formula I wherein $R^3$ is hydrogen (hereinafter referred to as an acid of formula I) is esterified.

The esterification may be carried out by any general procedure known for the preparation of analogous compounds.

Thus, an acid of formula I, or a reactive derivative thereof, may be reacted with a (1–4C)alkanol, for example methanol or ethanol.

When a reactive derivative is used, the process is preferably carried out in the presence of a suitable base, for example pyridine or triethylamine, and, conveniently, in an inert solvent, for example chloroform, methylene chloride, diethyl ether or tetrahydrofuran, and at a temperature of, for example, 0° to 100° C., and preferably, at 15° to 30° C. A particularly suitable reactive derivative of an acid of formula I is, for example, an acid halide such as an acid chloride or bromide, an acid azide, an acid anhydride, or a mixed anhydride derived from an acid of formula I and a (1–4C)alkanoic acid, such as acetic anhydride.

When an acid of formula I is used as starting material the esterification may be carried out:

(i) in the presence of a condensing agent such as dicyclohexylcarbodiimide, preferably under essentially anhydrous conditions and at a temperature of, for example, 15° to 30° C., for an extended period and in an inert solvent as defined above; or (ii) in the presence of a strong acid catalyst such as sulphuric, hydrochloric or toluene p-sulphonic acid, and in which case the (1–4C)alkanol may conveniently be used in excess and the process may conveniently be carried out at the boiling point of the reaction mixture, for example at 40° to 100° C.

Alternatively, the esterification may be carried out by reaction of an acid of formula I with the appropriate diazo-(1–4C)alkane, for example diazomethane. In which case, the process is preferably carried out in an inert diluent or solvent, for example diethyl ether, dimethoxyethane or tetrahydrofuran, and at a temperature of, for example, 15° to 30° C.

Whereafter, when a pharmaceutically acceptable base-addition salt of an acid of formula I is required, said acid is reacted using conventional procedures with the required base affording a pharmaceutically acceptable cation; and when an optical isomer is required the racemic form of an acid of formula I is resolved by reaction with an optically active base, for example (+) or (−)-α-methylbenzylamine, and then if required, subsequently esterified by process (d) hereinabove, or one of processes (a)-(c) is carried out using an optically active starting material.

As stated above, the compounds of formula I possess useful anti-arthritic properties, which may be demonstrated by the following standard laboratory procedure based on that devised by Newbould (*Brit. J. Pharmacol.* 1963, 21, 127–136). The procedure involves inducing arthritis in rats by intradermal injection of a suspension of heat-killed tubercle bacilli in paraffin oil into one hind foot pad of each rat, and then measuring the effects of daily oral dosing of a test compound on the increase in thickness of the injected foot, and on the inhibition of the rise of $\alpha_1$-acid glycoproteins in the blood serum, in both cases after at least 28 days. Using this test procedure the compounds of formula I produce significant activity at a daily dose of 100 mg./kg. or less, and without any overt toxic effects. Thus, by way of example only, the compound (±)-2-[4-(4-chlorophenyl)benzyloxy]-2-phenylbutyric acid produced a 38% inhibition of the increase in foot thickness and a 47% inhibition of the rise in serum $\alpha_1$-glycoprotein level after 28 days oral dosing at a daily rate of 80 mg./kg., without any overt toxic or other untoward effects being observed. Similarly, no such untoward effects were observed following 14 days oral dosing to normal rats at 300 mg./kg. with the same compound.

As stated above the compounds of formula I also possess desirable pharmacokinetic properties, for example as indicated by their relatively short elimination half-life from the blood serum in laboratory animals. Thus, by way of example only, the compound (±)-2-[4-(4-chlorophenyl)benzyloxy]-2-phenylbutyric acid has a serum elimination half-life of about 10 hours in rats whereas the known compound 2-[4-(4-chlorophenyl)-benzyloxy]-2-methylpropionic acid has a half-life of about 5 days in rats.

A relatively short elimination half-life is of particular importance since it enables a therapeutic serum level of compound to be achieved rapidly using a simple dosage regime involving dosing at regular intervals of less than 1 day between individual doses. Equally, in the event of any adverse, compound related reaction occurring, a relatively short serum elimination half-life ensures that the serum level falls rapidly to an acceptable level on cessation of dosing.

Whilst not wishing to be bound by any particular theory as to the mode of action of the compounds of formula I, it is considered that their activity is due to a fundamental effect on the arthritic disease processes producing the tissue damage rather than to a mere palliative effect on the resultant inflammation produced by the arthritis.

It is therefore envisaged that the compounds of the invention will be of value in the treatment of other diseases of connective tissues, such as atherosclerosis, in addition to their use in the treatment of arthritic joint diseases such as rheumatoid arthritis, psoriatic arthritis, and ahkylosing spondilitis.

When used to produce anti-arthritic effects in warm-blooded animals, the compounds of formula I will generally be administered at a daily oral dose in the range, for example 5 to 100 mg./kg. By way of example, in man this is likely to result in a total daily dose of from 125 to 2500 mg. given if necessary in divided doses.

The compounds of the invention may be administered in the form of pharmaceutical compositions and according to a further feature of the invention there is provided a pharmaceutical composition which comprises a compound of formula I in pharmaceutically acceptable form.

By "pharmaceutically acceptable form" is meant either a pharmaceutical preparation in which the compound is associated with a pharmaceutically acceptable diluent, or a pharmaceutical preparation, for example a capsule, in which the compound is confined in a unit dosage form without necessarily being associated with a diluent.

Preferred pharmaceutically acceptable forms are those suitable for oral administration for example tablets, capsules, suspensions, solutions, syrups or elixirs. However forms suitable for parenteral administration, for example sterile aqueous injections or suppositories, may also be employed. The compositions may be obtained by conventional procedures and, if desired, using conventional diluents or excipients. Dosage forms should preferably contain from 50 to 500 mg. of compound of a formula I per dosage unit.

When used in the treatment of inflammatory joint diseases the compositions of the invention may also contain one or more additional agents which can have a beneficial effect on the disease or on associated conditions, for example an agent selected from the following:

an anti-inflammatory or analgesic agent, for example, acetyl-salicylic acid, paracetamol, dextropropoxyphene, codeine, phenylbutazone, indomethacin, ibuprofen, ketoprofen, naproxen or sulindac;

an anti-inflammatory steroid, for example prednisolone;

an organo-gold derivative;

a uricosuric agent, for example probenecid;

chloroquine; and D-pencillamine.

The invention is illustrated by the following non-limiting Examples in which:

(i) all evaporations, unless otherwise stated, were carried out by rotary evaporation in vacuo;

(ii) reactions stated as carried out at room temperature were performed at a temperature of 18°–25° C.;

(iii) yields (where given) are purely illustrative and are not to be construed as the maximum attainable for the process illustrated; and (iv) all compounds are in racemic (±) form unless indicated otherwise.

EXAMPLE 1

A solution of ethyl 2-[4-(4-chlorophenyl)benzyloxy]-2-phenylpropionate (7.9 g.) in methanol (100 ml.) containing potassium hydroxide (11.0 g.) was heated under reflux for 2 hours and then evaporated. The residue was partitioned between water (100 ml.) and ether (30 ml.). The aqueous phase was separated and acidified with 4 N-hydrochloric acid to pH 2–3 and extracted with ether (3×30 ml.). These ether extracts were washed with water, dried (MgSO$_4$) and evaporated. The residue was crystallised by treatment with a mixture of ethyl acetate and hexane to give 2-[4-(4-chlorophenyl)-benzyloxy]-2-phenylpropionic acid, (3.5 g.), m.p. 125°–126° C.

The above mentioned substituted propionate was obtained as follows:

Sodium hydride (1.05 g., 50% w/w dispersion in mineral oil), was added to a stirred solution of ethyl 2-hydroxy-2-phenylpropionate (3.48 g.) at 4° C. in dimethylformamide (100 ml.). After 1 hour, 4-(4-chlorophenyl)benzyl chloride (4.74 g.) was added and stirring was continued at 4° C. for 1 hour and then at room temperature for 20 hours. The mixture was neutralised by cautious addition of N-hydrochloric acid and then extracted with ether. The extracts were washed with water, dried (MgSO$_4$) and evaporated to give ethyl 2-[4-(4-chlorophenyl)benzyloxy]-2-phenylpropionate as an oil (7.9 g.).

EXAMPLE 2

Using a similar procedure to that described in Example 1 there was obtained 2-[4-(4-chlorophenyl)benzyloxy]-2-phenylbutyric acid as a solid in 53% overall yield, m.p. 128°–130° C. (after recrystallisation from ethyl acetate/hexane) using methyl 2-hydroxy-2-phenylbutyrate instead of ethyl 2-hydroxy-2-phenylpropionate, and with the intermediate isolation of the ester methyl 2-[4-(4-chlorophenyl)benzyloxy]-2-phenylbutyrate as an oily solid of satisfactory purity.

EXAMPLE 3

Mandelic acid (12.16 g.) was added to a stirred suspension of sodium hydride (8.44 g., 50% w/w dispersion in mineral oil) in dimethyl sulphoxide (100 ml.) at 15°–20° C., and the mixture was then stirred at the same temperature for 4 hours. 4-(4-Chlorophenyl)benzyl chloride (18.96 g.) was added to the mixture and stirring was continued at room temperature for 20 hours.

The resultant mixture was adjusted to pH 1–3 by cautious addition of N-hydrochloric acid, and then extracted thoroughly with ether. The combined extracts were washed with water, dried (MgSO$_4$) and evaporated. The solid residue obtained was recrystallised from a mixture of ethyl acetate and hexane to give 2-[4-(4-chlorophenyl)benzyloxy]-2-phenylacetic acid (22.2 g.), m.p. 136°–137° C.

EXAMPLE 4

(+)-Mandelic acid (3.04 g.) was added to a stirred suspension of sodium hydride (1.92 g., 50% w/w dispersion in mineral oil) in dimethyl sulphoxide (50 ml.) at 15°–20° C., and the mixture was then stirred at the same temperature for 4 hours. 4-(4-Chlorophenyl)benzyl chloride (4.74 g.) was then added to the mixture and stirring was continued at room temperature for 1 hour. The resultant mixture was adjusted to pH 1–3 by careful addition of N-hydrochloric acid, and then extracted thoroughly with ether. The combined extracts were washed with water, dried (MgSO$_4$) and evaporated. The solid residue obtained was recrystallised from a mixture of ethyl acetate and hexane to give (+)-2-[4-(4-chlorophenyl)benzyloxy]-2-phenylacetic acid (3.45 g.), m.p. 119°–121° C., $[\alpha]_D^{25}$ +104° (C=1,CHCl$_3$).

EXAMPLE 5

Using a similar procedure to that described in Example 4 but starting with (−)-mandelic acid, there was obtained (−)-2-[4-(4-chlorophenyl)benzyloxy]-2-phenylacetic acid (2.23 g.), m.p. 120°–121° C., $[\alpha]_D^{25}$ −104° (C 2.1, CHCl$_3$).

EXAMPLE 6

Using a similar procedure to that described in Example 3 there was obtained 2-[4-(4-chlorophenyl)benzyloxy]-2-(4-chlorophenyl)acetic acid, m.p. 120°–122° C., in 45% yield starting from 4-chloromandelic acid and 4-(4-chlorophenyl)benzyl chloride.

EXAMPLE 7

A solution of 2-[4-(4-chlorophenyl)benzyloxy]-2-phenylacetic acid (8.0 g.) in ethanol (200 ml.) containing concentrated sulphuric acid (1 ml.) was heated under reflux for 90 minutes, then cooled to room temperature, and carefully neutralised by addition of an excess of saturated aqueous bicarbonate solution. The mixture obtained was evaporated and the residue extracted thoroughly with ethyl acetate. The combined extracts were washed with water, dried (MgSO$_4$) and evaporated to give ethyl 2-[4-(4-chlorophenyl)benzyloxy]-2-phenylacetate (6.65 g.), m.p. 50°–51° C.

EXAMPLE 8

Using a similar procedure to that described in Example 1, there was obtained from S-(+)-methyl 2-hydroxy-2-phenylbutyrate and 4-(4-chlorophenyl)benzyl chloride, S-(−)-2-[4-(4-chlorophenyl)benzyloxy]-2-phenylbutyric acid in 15% overall yield, m.p. 115°–116° C., $[\alpha]_D^{25}$ −52.3 (C=1.098, chloroform), with intermediate isolation of the S-methyl ester.

The S-(+)-methyl 2-hydroxy-2-phenylbutyrate was obtained by the procedure of McKenzie and Ritchie (*Chem. Ber.*, 1937, 70, 23), and the absolute configuration assignment is based on the absolute configuration of S-(+)-2-hydroxy-2-phenylbutyric acid determined by Mitsui et alia (*Chemistry and Industry*, 1964, 333).

EXAMPLE 9

(+)-α-Methylbenzylamine (67 ml.) was added to a solution of (±)-2-[4-(4-chlorophenyl)benzyloxy]-2-phenylbutyric acid (200 g.) in ethanol (1.4 l.). After 18 hours at room temperature the solid which had separated was collected by filtration and both the solid and the filtrate (A) were retained. The solid was recrystallised twice from ethanol and then shaken with 2 M sulphuric acid (800 ml.). The mixture obtained was extracted with ether (1.2 l.) and the extract washed with water, dried (MgSO$_4$) and then evaporated. The solid residue was recrystallised from a mixture of ethyl acetate and hexane to give S-(−)-2-[4-(4-chlorophenyl)benzyloxy]-2-phenylbutyric acid (36.0 g., in two crops) m.p. 116°–117° C., $[\alpha]_D^{25}$ −55.5° (C=1, chloroform).

EXAMPLE 10

The filtrate (A) obtained in Example 9 was shaken with 2 M sulphuric acid (1 l.) and the mixture extracted with ether (0.8 l.). The extract was washed with water, dried (MgSO$_4$) and evaporated. The residue obtained (120 g.) (containing both racemic (±)- and (+)-forms of 2-[4-(4-chlorophenyl)benzyloxy]-2-phenylbutyric acid) was dissolved in ethanol (1 l.). (−)-α-Methylbenzylamine (50 ml.) was added to the subsequent solution. After 18 hours at room temperature the solid which had formed was collected by filtration, and recrystallised twice from ethanol. The crystalline material obtained was suspended in 2 M sulphuric acid and the mixture extracted with ether in a similar manner to that described in Example 9. There was thus obtained from the dried ether extract, R-(+)-2-[4-(4-chlorophenyl)benzyloxy]-2-phenylbutyric acid (30.9 g., in two crops), m.p. 117°–118° C., $[\alpha]_D^{25}$ +54.5° (C=1, chloroform), after recrystallisation from a mixture of ethyl acetate and hexane.

EXAMPLE 11

A solution of diazomethane in ether (100 ml.) (obtained by a standard procedure by reaction of bis(N-methyl-N-nitroso)terephthalamide (5 g.) with an excess of ethanolamine followed by distillation of the ethereal diazomethane solution) was added to a solution of 2-[4-(4-chlorophenyl)benzyloxy]-2-phenylbutyric acid (4.0 g.) in ether (100 ml.). After 2 hours at room temperature the mixture was evaporated and the oily residue was purified by chromatography on a column of silica gel (200 g.) using a mixture containing 1 part by volume of ethyl acetate to 4 parts by volume of toluene as eluant. The starting substituted butyric acid was not eluted by this solvent system. Accordingly evaporation of the eluate gave methyl 2-[4-(4-chlorophenyl)benzyloxy]-2-phenylbutyrate (2.5 g.), m.p. 68°-72° C.

EXAMPLE 12

Sodium hydride (3.16 g. of a 50% w/w dispersion in mineral oil) was added in portions to a stirred solution of 2-hydroxy-2-phenylpropionic acid (4.98 g.) in dimethyl sulphoxide (100 ml.). After 2 hours stirring at room temperature, 4-(4-chlorophenyl)benzyl chloride (9.5 g.) was added and stirring was continued for 20 hours. The mixture was then carefully treated with water (200 ml.) and ether (200 ml.) to give the sodium salt of 2-[4-(4-chlorophenyl)benzyloxy]-2-phenylpropionic acid as an insoluble solid. This solid was collected by filtration and treated with a mixture of ethyl acetate (200 ml.) and 4 M hydrochloric acid (200 ml.). The organic phase was separated, washed with water, dried (MgSO$_4$) and evaporated. The solid residue obtained was recrystallised from a mixture of ethyl acetate and hexane to give 2-[4-(4-chlorophenyl)benzyloxy]-2-phenylpropionic acid (5.35 g.), m.p. 127°-130° C.

EXAMPLE 13

A solution containing sodium hydroxide (0.407 g.) in water (10.25 ml.) was added to a stirred suspension of 2-[4-(4-chlorophenyl)benzyloxy]-2-phenylbutyric acid (4.0 g.) in water (100 ml.). The mixture was stirred for 15 minutes and then undissolved material removed by filtration. The filtrate was evaporated. The residual solid was further evaporated with toluene (2×20 ml.) and then dried in vacuo over phosphorous pentoxide at 90° C. to constant weight. There was thus obtained sodium 2-[4-(4-chlorophenyl)benzyloxy]-2-phenylbutyrate (3.95 g.); microanalysis: found: C, 68.2, H, 5.1%; $C_{23}H_{20}ClNaO_3$ requires: C, 68.57, H, 5.0%.

EXAMPLE 14

Using a similar procedure to that described in Example 13, but replacing sodium hydroxide by a solution of potassium hydroxide (0.576 g.) in water (14.8 ml.), there was obtained potassium 2-[4-(4-chlorophenyl)benzyloxy]-2-phenylbutyrate (3.7 g.); microanalysis: found: C, 65.9; H, 4.9%; $C_{23}H_{20}ClKO_3$ requires: C, 65.93; H, 4.81%.

EXAMPLE 15

Using a similar procedure to that described in Example 13, but replacing sodium hydroxide by a solution of tris(hydroxymethyl)methylamine (1.211 g.) in water (10 ml.) and using 3.81 g. of 2-[4-(4-chlorophenyl)benzyloxy]-2-phenylbutyric acid, there was obtained tris(hydroxymethyl)methylammonium 2-[4-(4-chlorophenyl)-benzyloxy]-2-phenylbutyrate (4.56 g.); microanalysis: C, 63.8; H, 6.3; N, 2.5%; $C_{27}H_{32}ClNO.0.25H_2O$ requires: C, 64.0; H, 6.4; N, 2.8%.

EXAMPLE 16

The procedure of Example 13 was repeated to give an aqueous solution of the sodium salt of 2-[4-(4-chlorophenyl)benzyloxy]-2-phenylbutyric acid. A solution of calcium chloride (0.564 g.) in water (50 ml.) was added to the aqueous solution. The dense precipitate which formed was collected by filtration and washed with water and then ethanol, and dried in vacuo over phosphorus pentoxide at 90° C. to constant weight to give calcium 2-[4-(4-chlorophenyl)benzyloxy]-2-phenylbutyrate (3.86 g.); microanalysis: found: C, 66.6; H, 5.2; Cl, 8.2%; $C_{46}H_{40}Cl_2O_6Ca.1.5H_2O$ requires: C, 66.8; H, 5.2; Cl, 8.6%.

EXAMPLE 17

An excess of ammoniacal methanol was added to a solution of 2-[4-(4-chlorophenyl)benzyloxy]-2-phenylbutyric acid (4.0 g.) in methanol (50 ml.). The subsequent mixture was evaporated and the residue obtained was recrystallised from a mixture of ether and hexane to give ammonium 2-[4-(4-chlorophenyl)benzyloxy]-2-phenylbutyrate (3.68 g.); microanalysis: found: C, 68.7; H, 6.1; N, 3.2%; $C_{23}H_{24}ClNO_3.0.25H_2O$ requires: C, 68.7; H, 6.1; N, 3.5%.

EXAMPLE 18 (all parts by weight)

A mixture of 100 parts of 2-[4-(4-chlorophenyl)benzyloxy]-2-phenylbutyric acid, 100 parts of lactose and 50 parts of maize starch was granulated with a sufficient quantity of a 5% aqueous solution of polyvinylpyrrolidone. The granulated material obtained was sieved through a 1400μ (12 mesh) screen and then dried at 50°-60° C. The dried material was then passed through a 1000μ (16 mesh) screen, and then mixed with 2.5 parts of magnesium stearate. The mixture was then compressed in conventional manner to give tablets suitable for oral administration for therapeutic purposes.

EXAMPLE 19

The procedure described in Example 18 may be repeated using as active ingredient another compound of the invention or, where appropriate, a base-addition salt as described in the preceding Examples 2-17.

What is claimed is:

1. A hydroxyacetic acid derivative of the formula:

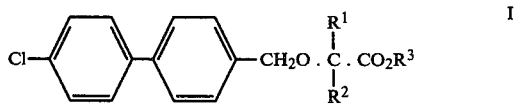

wherein $R^1$ is hydrogen or a (1-4C)alkyl radical, $R^2$ is a phenyl radical optionally bearing a halogeno radical, and $R^3$ is hydrogen or a (1-4C)alkyl radical; or when $R^3$ is hydrogen, a pharmaceutically acceptable base-addition salt thereof.

2. A compound as claimed in claim 1 wherein $R^1$ is hydrogen, a methyl or ethyl radical, $R^2$ is a phenyl radical optionally bearing a fluoro, chloro or bromo radical, and $R^3$ is hydrogen, a methyl or ethyl radical.

3. A compound as claimed in claim 1 wherein $R^2$ is a phenyl or 4-chlorophenyl radical, and $R^3$ is hydrogen, a methyl or ethyl radical.

4. A compound as claimed in claim 1 wherein $R^1$ is a methyl or ethyl radical, $R^2$ is a phenyl radical, and $R^3$ is hydrogen, a methyl or ethyl radical.

5. A compound as claimed in claim 1 wherein $R^3$ is hydrogen.

6. 2-[4-(4-Chlorophenyl)benzyloxy]-2-phenylpropionic acid, or a pharmaceutically acceptable base-addition salt thereof.

7. 2-[4-(4-Chlorophenyl)benzyloxy]-2-phenylbutyric acid, or a pharmaceutically acceptable base-addition salt thereof.

8. A pharmaceutically acceptable base-addition salt of a compound of formula I as claimed in claim 1 which is an alkali metal or alkaline earth metal salt, an aluminium salt, or a salt of an organic base affording a pharmaceutically acceptable cation.

9. A pharmaceutical composition having anti-arthritic properties which comprises an effective amount of a compound of formula I or a pharmaceutically acceptable base-addition salt thereof, as claimed in claim 1, together with a pharmaceutically acceptable diluent or carrier.

10. A pharmaceutical composition as claimed in claim 9 wherein the active ingredient is 2-[4-(4-chlorophenyl)-benzyloxy]-2-phenylbutyric acid, or a pharmaceutically acceptable base-addition salt thereof.

11. A method of producing an anti-arthritic effect in a warm-blooded animal requiring such treatment which comprises administering to said animal an effective amount of a compound of formula I or a pharmaceutically acceptable base-addition salt thereof as defined in claim 1.

* * * * *